United States Patent [19]

Shahbabian

[11] 4,312,353
[45] Jan. 26, 1982

[54] METHOD OF CREATING AND ENLARGING AN OPENING IN THE BRAIN

[75] Inventor: Set Shahbabian, Cincinnati, Ohio

[73] Assignee: Mayfield Education and Research Fund, Cincinnati, Ohio

[21] Appl. No.: 148,410

[22] Filed: May 9, 1980

[51] Int. Cl.³ ............................................. A61M 29/02
[52] U.S. Cl. .................................. 128/344; 128/1 R; 128/20
[58] Field of Search ................... 128/349 B, 344, 348, 128/20, 1 R

[56] References Cited

U.S. PATENT DOCUMENTS 1,735,519 11/1929 Vance .................................. 128/344
3,799,170 3/1974 Walsh et al. ......................... 128/344

FOREIGN PATENT DOCUMENTS 512456 9/1939 United Kingdom ............ 128/349 B

OTHER PUBLICATIONS

George Tiemann & Co.'s Surgical Instruments, 1889 Catalogue, p. 504.

Primary Examiner—Gene Mancene
Assistant Examiner—Mickey Yu
Attorney, Agent, or Firm—Wood, Herron & Evans

[57] ABSTRACT

The method of creating and enlarging an opening in the brain with minimal damage to nerve tissue. A catheter consisting of a stylette surrounded by an inflatable sac having a rounded tip is very gently inserted into the brain. When inserted a distance up to about 2½ inches, the sac is inflated by gradually injecting fluid into the sac to gently expand it, thereby pushing aside nerve bundles with a minimum of damage to the nerve bundles. After a hole, usually oblong and having a maximum dimension of about 2½ inches, is created, the catheter is withdrawn and retractors are employed to maintain the opening until surgery is performed within the brain.

6 Claims, 5 Drawing Figures

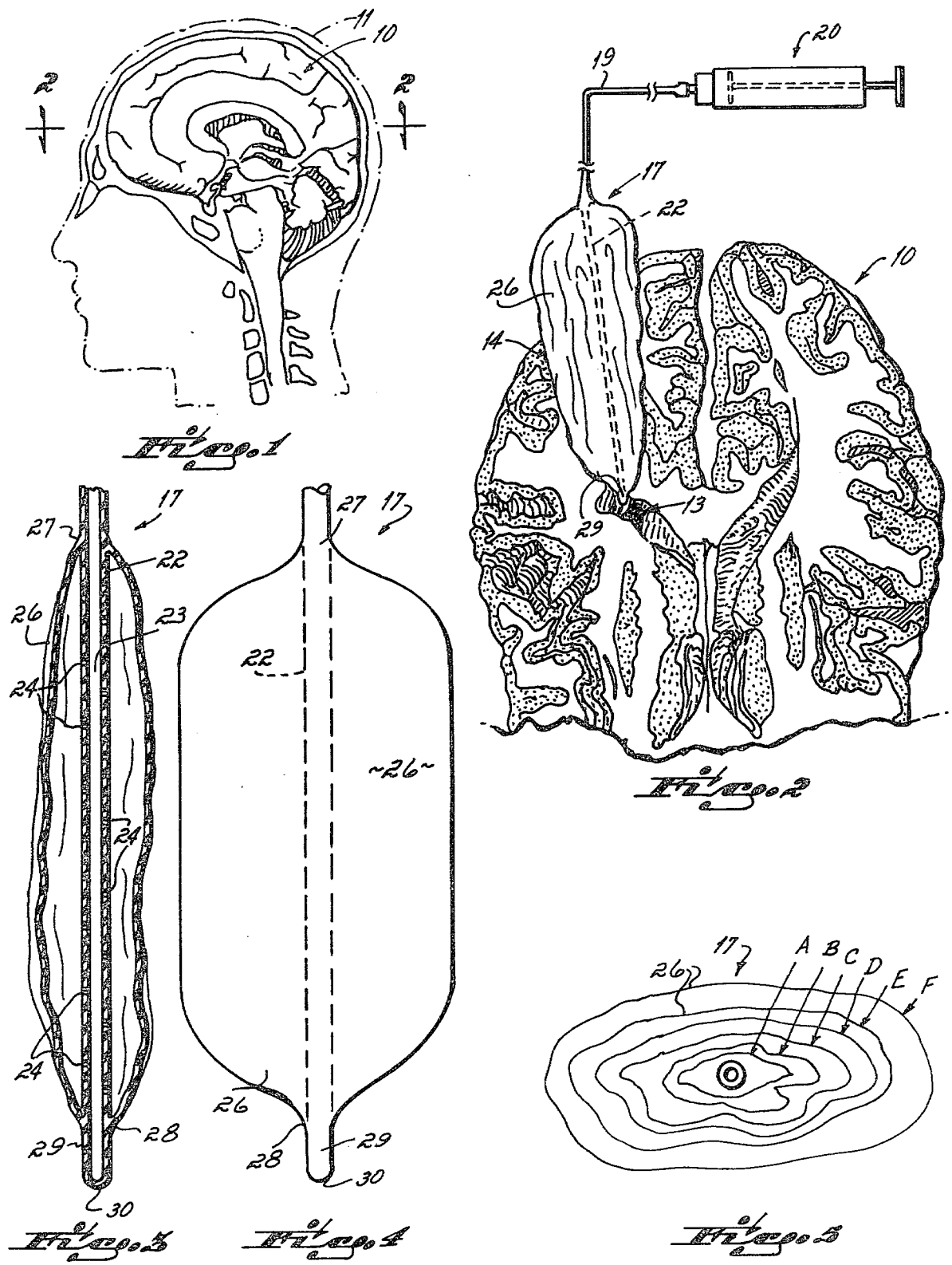

METHOD OF CREATING AND ENLARGING AN OPENING IN THE BRAIN

This invention relates to a method of creating an opening in the brain to permit surgical operations to be performed.

Among other things, the brain consists of nerve bundles surrounded by connective tissue (glial). The nerve tissue is generally stronger and more resistant to rupture than the connective tissue. Prior to the present invention, surgery on the brain (for example, to remove a tumor within the brain) required the cutting of an opening in the brain with a scalpel. In the process of creating a hole large enough to permit access to the tumor, an extraordinary amount of nerve tissue had to be severed, thereby creating permanent injury to the brain.

The objective of the present invention is to provide a method of creating a large opening in the brain with a minimum of damage to nerve tissue in the area of the brain around the opening.

This objective of the invention is attained by providing a catheter consisting of a stiff stylette of about 3 mm in diameter and surrounding it by a very thin, inflatable sac, the sac having means for supplying fluid, preferably a saline solution, thereto.

After a hole in the skull is formed, the catheter is very gently and slowly inserted into the brain. In moving slowly through the brain, the rounded end of the catheter moves through the connective tissue, very gently thrusting aside the connective tissue as well as nerve bundles. While some nerve tissue is ruptured by the passage of the catheter into the brain, the destroyed nerve tissue is an extremely small percentage of that which is destroyed by cutting.

When the catheter has penetrated to the desired depth into the brain, the saline solution is gently pumped by means of a syringe into the sac to inflate or dilate it. The inflating process occupies a time period of about 10–15 minutes. The first injection of fluid might be approximately 0.2 cc. That is withdrawn and then 0.3 cc is introduced. The process is continued by alternately inflating and deflating the sac, the inflating being with ever increasing amounts of fluid.

The very thin walled sac will, during this process, send out tentacles of sac material through the less resistive connective tissue surrounding the nerve fibers. As additional amounts of fluid are introduced, the sac around the stylette expands and the tentacles expand, all of which gradually form an opening by pushing aside connective tissue until the sac is completely expanded to an oval-shaped cross section having a maximum dimension of about 2 inches and a minimum dimension of about 1½ inches. Thereafter, the catheter is removed and retractors put in place to hold the opening to the desired size until surgery is completed.

The invention will be more completely understood by reference to the accompanying drawings in which:

FIG. 1 is a somewhat schematic view generally in sagittal section of a human head and neck;

FIG. 2 is a somewhat schematic view in section of a portion of the brain taken along the line 2—2 of FIG. 1, a catheter constructed in accordance with an embodiment of this invention being shown in association therewith;

FIG. 3 is a coronal section view of the catheter in collapsed position;

FIG. 4 is a view in side elevation of the catheter in distended position; and

FIG. 5 is a diagrammatic illustration of the stages of inflation through which the sac passes.

A human head is shown in FIG. 1, the head having a brain 10 enclosed by a skull 11. The brain is illustrated diagrammatically in FIG. 2. The brain consists of, among other things, nerve tissues joined by connective tissue (glial). The brain may have a tumor 13 located at some depth into the brain from its surface which must be surgically removed. It is necessary to form a passageway 14 into the brain to the tumor 13 so that the tumor can be surgically removed. The device for creating the passageway is illustrated at 17 and in detail in FIGS. 1–4. The device 17 is a catheter which is connected by a tube 19 to a syringe 20 containing a fluid such as a saline solution. The saline solution may be introduced into the catheter by means of the syringe which drives the fluid under gentle pressure through the tube 19.

As shown in FIGS. 3 and 4, the catheter is formed of a stiff rubber stylette 22 having a longitudinal passageway 23 and a series of transverse or radial passageways 24 connecting the interior passageway 23 to the exterior of the stylette. A very thin flexible sac 26 is connected at its upper end 27 and its lower end 28 in fluid-tight fashion to the stylette. The sac is preferably about the thinness and flexibility of a condom and may be joined as by vulcanizing or other means to the rubber stylette. The stylette is about 3 mm in diameter and has an end portion 29 projecting slightly beyond the lower end 28 of the sac 26. The projecting end 29 has a rounded end 30.

In the method of creating a passageway into the brain, the surgeon first cuts an opening in the skull in the usual way. When the brain is exposed, the surgeon inserts the rounded tip 30 of the catheter into the brain and gently passes it through the connective tissue while pushing aside the stronger nerve tissue. To some extent the end 29 with the rounded tip 30 of the catheter will tend to seek the path of least resistance through the connective tissue and around the nerve tissue or nerve bundles. More probably, the action is primarily a thrusting aside of the nerve bundles as the catheter noses its way through the connective tissue. While some nerve tissue will necessarily be ruptured during this passage, the damage is minimal compared to that which was required when a surgical knife for access to the tumor was used.

When the catheter is inserted to the desired extent, up to about 2½ inches, the surgeon gently introduces the saline solution into the sac via the longitudinal passageway 23 and the transverse passageways 24. The saline solution might initially be introduced in a quantity of 0.2 cc. That solution would be withdrawn and a second, slightly larger amount, e.g., 0.3 cc, is introduced. A portion of that solution is withdrawn and thereafter a slightly greater amount is introduced. This operation of continuously inflating and deflating alternately is continued for about 10–15 minutes until the passageway is enlarged to the desired size. The sensitive touch of the surgeon will be used to ascertain that during inflation the sac is pushing tissue aside rather than rupturing it.

The very flexible sac will move into the tissue in tentacle fashion. During the course of its inflation, it might assume a series of cross sectional configurations illustrated diagrammatically in FIG. 5 at A, B, C, D, E, F. These configurations are highly irregular and are illustrative of the fact that with the very gently pressure slowly applied to the sac, the sac will seek out paths of least resistance through the connective tissue and around the nerve bundles and very gently crowd the connective tissue and nerve bundles generally radially away from the stylette until a passageway of substantial size has been created. As shown at F, the passageway tends to be generally oval-shaped in cross section, having a maximum dimension of about 2 inches and a minimum dimension of about 1½ inches.

After the passageway has been created, the catheter is removed and retractors positioned in place to hold the tissue in place while surgery is performed.

I claim:

1. The method of forming an opening in the brain with minimal damage to nerve tissue, comprising the steps of,
    inserting into the brain a catheter formed by a stylette surrounded by a thin, inflatable sac, said catheter having a projecting end approximately 3 mm in diameter, said end being tapered,
    easing said catheter through the brain connective tissue and past said nerve tissue, and
    gradually injecting a fluid into said inflatable sac to gently expand it, thereby pushing aside nerve tissue with minimal damage to the nerve tissue.

2. The method as in claim 1 in which the step of injecting fluid into said sac comprises,
    first injecting a small quantity of fluid,
    withdrawing at least a portion of said fluid,
    injecting a total quantity of fluid greater than said first quantity,
    and repeating said steps of alternately injecting and withdrawing while gradually increasing the total quantity of fluid in said sac.

3. The method as in claim 1 in which said catheter is inserted up to about 2.5 inches into the brain.

4. The method as in claim 1 in which said sac is expanded to a maximum radial dimension of about 2 inches.

5. The method as in claim 1 in which said sac is expanded after complete penetration into said brain.

6. The method as in claim 1 comprising the further steps of removing said catheter after it has been expanded, and applying retractors to the opening created by the catheter.

* * * * *